United States Patent [19]

Holtkamp

[11] Plant 4,550

[45] Jun. 17, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 15,825

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African violet known by the varietal name Manitoba and characterized by its light blue, violet-shaped single flowers, having violet blue centers; dark green shiny leaves; vigorous growth habit; with 7 to 9 flower stems producing 7 or more single flowers when the plant is in full bloom, and by its early and continuous blooming.

1 Drawing Figure

1

The present invention comprises a new and distinct cultivar of African violet plant, botanically known as *Saintpaulia ionantha,* and hereinafter referred to by the cultivar name Manitoba.

The new cultivar referred to during the breeding and selection process by the designation C56/1-2/79, is a product of a planned breeding program. The new cultivar is generally characterized by its light blue, violet-shaped single flowers; dark green, very shiny and attractive leaves; essentially continuous blooming, even during brief periods where the plant has only 2 or 3 flower stems, and by its 7–9 flower stems with 7 and more single flowers on each stem. These traits in combination were not present in previously available commercial cultivars.

The new cultivar was originated from a cross made in a controlled breeding program in Isselburg, Rhineland, Germany. The female, or seed parent was a cultivar designated XVII 512 Lilac, an unpatented cultivar. The male, or pollen parent was a cultivar designated XXI 1 Frue Light blue, similarly not patented.

The new cultivar Manitoba was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of as asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Manitoba which in combination distinguish this African violet as a new and distinct cultivar:

1. Single flowers, violet-shaped, light blue in color except for centers which are violet blue.
2. Attractive dark green, shiny leaves, generally heart-shaped and slightly hairy.

2

3. 7 to 9 flower stems, each producing 7 or more single flowers, with the flowers appearing in the center well above the foliage.
4. Vigorous growth habit.
5. Flexible peticels.
6. Early (5–6 weeks after potting) and continuous blooming.

The accompanying photographic drawing shows a typical speciment plant of the new cultivar. The colors appearing in the photograph are as true as possible with color illustrations of this type.

In the following description, color references are made both to the Royal Horticultural Society color chart (RHS) and to the Horticultural Color Chart issued by Wilson Colour Ltd. (HCC). The values have been selected from these references in order to provide the most accurate readings.

Botanical classification: *Saintpaulia ionantha,* Ramat. cv Manitoba.

Parentage:

*Male parent.*—XXI 1 Frue Light blue.

*Female parent.*—XVII 512 Lilac.

Propagation: The new cultivar holds its distinguishing characteristics through successive propagations by leaf cuttings and by division of shoots.

Plant: From 7 cm. to 10 cm. tall when grown in pots, and approximately 25–30 cm. in diameter when fully grown.

Leaves:

*General form.*—Heart-shaped.

*Diameter.*—60–70 mm.

*Texture.*—Soft.

*Aspect.*—Very shiny; hairy, with smooth edges.

*Veins.*—Visible on upperside, on underside well pronounced.

*Color (upperside).*—RHS 147A.

*Color (underside).*—HCC 30/2 (cyclamen purple).

*Petiole.*—Greenish-brown to dark reddish-brown.

Flowers:

*Buds.*—Bell-shaped; 7 mm. in diameter just before opening, color RHS 85D Violet.

*Sepals.*—Color: 177D RHS Greyed orange. Calyx; seed bud grown together with receptacle and pushed slightly through. Aspect: funnel shaped. Peduncle: short and strong.

Individual flowers:

*Size.*—Up to 60 mm. in diameter, flat funnel.

*Color.*—Upperside: RHS 91A Violet blue. Underside: RHS 92B Violet blue. the center of the flower is darker, color RHS 93B Violet blue.

*Borne.*—Each stem carries 7–9 single flowers.

*Shape.*—Violet-shaped, 2 small and 3 large petals with smooth edges.

*Arrangement.*—Flowers are on slightly bent flower stems.

*Flowering time.*-In 5–6 weeks after potting, the first flowers appear. Thereafter, the plant is nearly always in bloom, with 9 or more flower stems appearing in full bloom.

Reproductive organs:

*Stamens.*—2 in number.

*Anthers.*—Four cells, color RHS 9A Yellow.

*Arrangement.*—Stamens are connected with receptacle on two short flat stems.

*Filaments.*—Greenish-yellow, 3–4 mm. long.

*Styles.*—8 mm. long, slightly bent, color RHS 93B.

*Pollen color.*—RHS 18C.

Roots: Normal developed, strong main root; small velvety branches, white when young, turning brownish when older.

Disease resistance: No disease problems noticed to date.

General observations: Manitoba has the very valuable attribute of early and continuous flowering. The first flowers appear relatively quickly (5–6 weeks) after potting, and thereafter the plant is in continuous bloom. This early and continuous blooming characteristic also appears in the cultivar Ontario, disclosed in my application filed concurrently herewith. Manitoba is distinguished from Ontario by several important characteristics, including flower color and quantity of flower production.

I claim:

1. A new and distinct cultivar of African violet, as shown and described, known by the varietal name Manitoba and characterized by the combined characteristics of light blue, violet-shaped single flowers, having violet blue centers; dark green shiny leaves; vigorous growth habit; with 7 to 9 flower stems producing 7 or more single flowers when the plant is in full bloom, and by its early and continuous blooming.

* * * * *

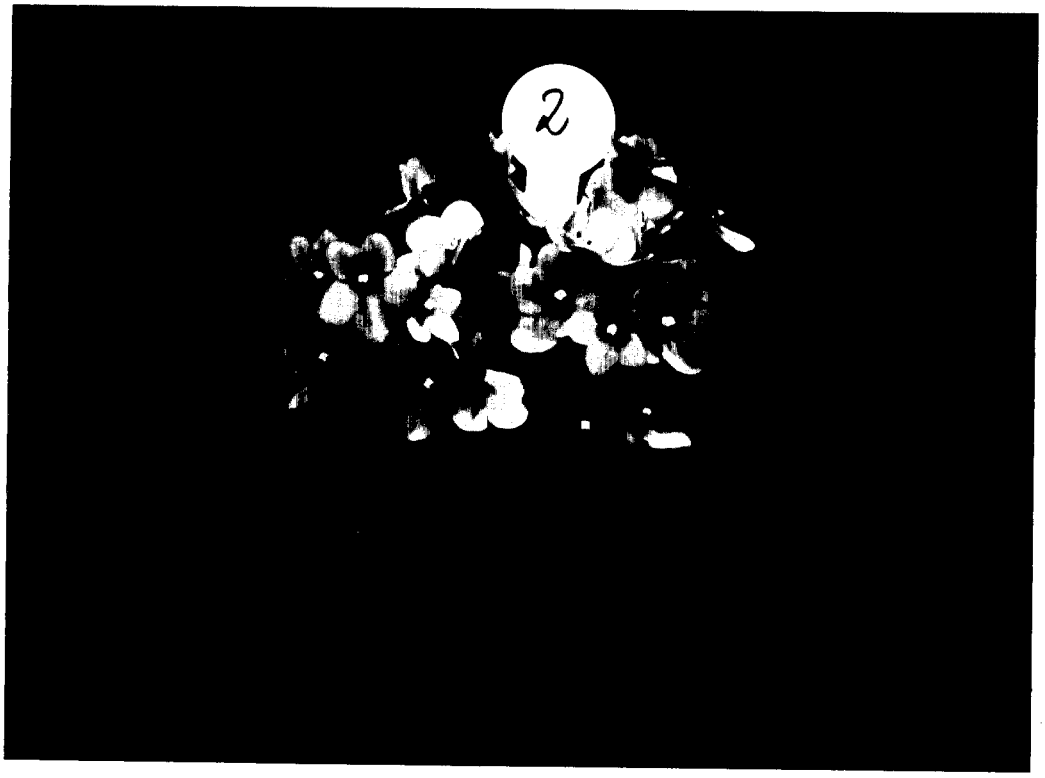
2